United States Patent [19]

White

[11] Patent Number: 5,455,100

[45] Date of Patent: Oct. 3, 1995

[54] POROUS ARTICLES AND METHODS FOR PRODUCING SAME

[75] Inventor: Eugene W. White, Rossiter, Pa.

[73] Assignee: Interpore International, Irvine, Calif.

[21] Appl. No.: 134,260

[22] Filed: Oct. 8, 1993

Related U.S. Application Data

[62] Division of Ser. No. 647,999, Jan. 30, 1991, Pat. No. 5,348,788.

[51] Int. Cl.[6] .................... A61F 2/02; B32B 3/20
[52] U.S. Cl. .................. 428/131; 428/134; 428/220; 428/213; 428/338; 428/304.4; 428/314.2; 428/315.5; 428/319.3; 428/166; 428/178; 428/137; 623/1; 623/8; 623/11; 623/16
[58] Field of Search ................... 428/131, 134, 428/220, 213, 338, 304.4, 314.2, 315.5, 319.3, 166, 178, 137; 623/1, 8, 11, 16

[56] References Cited

U.S. PATENT DOCUMENTS

| | | | |
|---|---|---|---|
| 3,788,024 | 1/1974 | Dettartog | 52/637 |
| 3,852,054 | 12/1974 | Wheeler et al. | 29/182 |
| 3,890,107 | 6/1975 | White et al. | 156/58 |
| 3,929,921 | 12/1975 | Wilke et al. | 260/666 A |
| 4,231,979 | 11/1980 | White et al. | 264/81 |
| 4,329,202 | 5/1982 | White et al. | 201/27 |
| 4,439,391 | 3/1984 | Hung | 264/317 |
| 4,722,870 | 2/1988 | White | 428/621 |
| 4,839,215 | 6/1989 | Starling et al. | 428/131 |
| 4,861,733 | 8/1989 | White | 501/1 |
| 4,976,736 | 12/1990 | White et al. | 623/16 |
| 4,978,355 | 12/1990 | Frey et al. | 623/16 |
| 5,030,233 | 7/1991 | Ducheyne | 623/16 |
| 5,147,402 | 9/1992 | Bohler et al. | 623/16 |
| 5,192,324 | 3/1993 | Kenna | 623/16 |
| 5,222,987 | 6/1993 | Jones | 623/16 |
| 5,282,861 | 2/1994 | Kaplan | 623/11 |
| 5,342,919 | 8/1994 | Dickens, Jr. et al. | 528/323 |

*Primary Examiner*—William P. Watkins, III
*Attorney, Agent, or Firm*—Hopgood, Calimafde, Kalil & Judlowe

[57] ABSTRACT

A porous article comprising a three-dimensional network of interconnecting pores and a void volume between twenty and eighty percent. The porous article is manufactured using a specifically delineated mesh structure wherein the pore size, void volume and material properties are tightly controlled and easily varied. The resulting material is advantageously applied to several bio-medical applications, including reconstructive surgery and arterial replacement.

7 Claims, 7 Drawing Sheets

L=SE1   EHT = 20.0 KV   WD =14 mm   M A G = X 100   PHOTO = 2
200 μm ⊢―――⊣   SURFACE   MESH

*F I G. 10*

L=SE1   EHT = 20.0 KV   WD =15 mm   M A G = X 100   PHOTO = 2
200 μm ⊢―――⊣   SURFACE   MESH

*F I G. 11*

L=SE1  EHT = 13.0 KV  WD =14 mm  M A G = X 50.0  PHOTO = 6
500 μm ⊢――――⊣  SILICONE REPLICATED SURFACE  MESH

*FIG. 12*

L=SE1  EHT = 13.0 KV  WD =15 mm  M A G = X 250  PHOTO = 14
50.0 μm ⊢――⊣  SILICONE REPLICATED SURFACE  MESH

*FIG. 13*

POROUS ARTICLES AND METHODS FOR PRODUCING SAME

This is a divisional of application Ser. No. 07/647,999, filed on Jan. 30, 1991, now U.S. Pat. No. 5,348,788.

The present invention generally relates to a select class of porous articles having a three-dimensional network of interconnecting pores, the mesh used to form selectively shaped porous articles, and processes for producing the mesh. The porous articles and underlying mesh of the present invention are specifically engineered for medical applications, such as arterial replacement and reconstructive bone surgery.

Disclosure Document No. 218,913 was filed on Jan. 30, 1989. The contents of this Disclosure Document are incorporated herein, as if restated in full.

BACKGROUND OF THE INVENTION

Porous materials are of paramount importance in many engineering disciplines. For centuries, woven fabrics have been applied to numerous filtration operations with the woven matrix impeding the passage of large suspended matter while permitting the flow of the suspending media. More recently, non-woven membranes characterized by tightly controlled pore size and distribution have been developed for use in ultrafiltration and reverse osmosis operations. These materials have a parallel pore network consistent with their flow-through objective.

Other porous structures have been designed for light weight structural support duty and are often applied in aerospace and aircraft construction, e.g., wing design. In these structures, the focus is on the managed translation of forces and loads throughout the structure. The ancillary network of pores associated with these designs are solely directed to the support of certain forces while minimizing the associated mass.

In the medical field, there has recently developed a need for porous articles for use in conjunction with certain medical procedures. These procedures include reconstructive surgery and repairing of highly comminuted fractures. The healing of a bone break can be accelerated by the inclusion of porous matrix adjacent to the break point, enhancing bone growth. In reconstructive surgery, a damaged bone, such as a tibia, is rebuilt. This often requires the insertion of a suitable prosthesis device to provide the desired shape.

A prosthesis device is an engineered element that achieves certain biological functions when placed within a living organism. An important class of prosthesis devices is directed to repair and/or replace human body elements, such as knee or hip joints. To replace a biological joint in an acceptable long lasting manner, the replacement element must join with the surrounding tissue. This is also true in applications of artificial skin and artificial blood vessels. The proper melding of the prosthesis is accomplished through the use of an appropriate material having a micro-network of capillaries permeating the structure to permit tissue ingrowth. The porous network must be continuous, permitting unrestricted passage of blood and linkage to the surrounding tissue, while providing a degree of structural support. This can be easily envisioned in the design of artificial blood vessels, wherein the vessel wall must support the forces associated with blood flow, while simultaneously passing oxygen, proteins and other extracellular matter to the surrounding tissue.

The porous materials providing the best blend of performance characteristics were first found in nature. Certain aquatic animals were discovered as having a micro-porous matrix. More specifically, the protoreaster (spiny starfish), slate pencil sea urchin and certain coral exhibit a solid structure formed of calcium carbonate having a network of interconnecting pores and significant void volume. For example, the slate pencil sea urchin has cigar-shaped protrusions that have a void volume of 50 percent, a porous structure with pore diameters of approximately 25 µm., and a mostly uniform structure exhibiting a mathematically minimal surface area. Certain coral provide similar attributes with pore diameters of approximately 250–600 µm.

In the past, these aquatic materials were used to form biologically acceptable structures by injecting silicone rubber into the porous matrix and then dissolving the calcium carbonate skeleton. Another technique involved the hydrothermal treatment of the calcium carbonate skeleton, forming hydroxyapatite (HA). A more detailed discussion of these techniques may be found in U.S. Pat. Nos. 3,929,971, 3,890,107, 4,231,979, 4,861,733 and 4,722,870; the teachings of which are incorporated herein by reference. Although these procedures offer a unique class of structures, they are accompanied by several significant drawbacks. As a first point, the naturally forming aquatic structures were never completely uniform and often exhibited imperfections detrimental to surgical implantation. In addition, the materials are expensive to harvest and have raised certain environmental concerns.

These problems have sparked a search for techniques to engineer and manufacture porous materials having specifically delineated structural properties in a controlled manner. The present invention is a result of this search.

OBJECTS AND SUMMARY OF THE PRESENT INVENTION

It is an object of the present invention to provide a porous article that has a three-dimensional network of interconnecting pores and a void volume percent between 20 and 80.

It is another object of the present invention to provide a porous article with a uniform distribution of pores wherein the pore diameter ranges between 25 and 1000 µm.

It is yet another object of the present invention to provide a structure formed of a biologically compatible material and tailored to specific system constraints.

It is a further object of the present invention to provide a non-woven mesh having a uniform pattern of openings and protrusions wherein the protrusions are of equal height extending outward from one surface of the mesh.

It is another object of the present invention to provide a method for manufacturing a non-woven mesh and select porous articles with predetermined structural characteristics based thereon.

The above and other objects of the present invention are realized in an illustrative porous article having a three-dimensional network of interconnecting pores. This article is prepared by first forming a non-woven mesh having a specifically delineated topographical surface structure and then stacking the mesh in alternating layers in a manner corresponding to the shape of the desired structure. A mandrel may be used to control the resulting shape pursuant to the layering operation.

In accordance with the varying aspects of the present invention, the methods for manufacturing the mesh involve the preparation of a form suitable for receiving curable materials such as silicone rubber. The form is machined to provide a topographical surface corresponding to the mirror image of the desired mesh. This includes the formation of a pattern of openings and protrusions of fixed diameter and height. This may be accomplished by various micro-surface machining techniques that are, per se, well known, such as photolithography and electron discharge machining.

The foregoing features of the present invention may be more fully appreciated by reference to the following detailed description of the specific embodiments thereof, in conjunction with the associated figures.

BRIEF DESCRIPTION OF THE FIGURES

FIG. 9 (A–C) provides a perspective view of sample blocks used as the repeating unit in the matrix of the present invention;

DETAILED DESCRIPTION OF THE PRESENT INVENTION

First briefly in overview, the present invention is directed to the preparation of a unique non-woven mesh and the porous articles based thereon. These articles resemble certain naturally occurring materials that have been harvested from an aquatic environment, such as the protoreaster (spiny starfish), slate pencil sea urchin and certain coral species. Notwithstanding this similarity, the porous articles of the present invention are man made and exhibit a uniformity of structure and specific design characteristics not found in nature. Therefore, the present invention is also directed to enhanced techniques of manufacturing these structures in a controlled and cost effective manner.

The generalized approach is to form a non-woven mesh in sheet stock form. This mesh has a uniform pattern of openings across its surface that extend through the sheet. In addition, this mesh has a uniform pattern of protrusions extending outward from the sheet's surface to a substantially constant height. These protrusions are distributed in a pattern that corresponds to the pattern associated with the openings, but offset therefrom, so that an even distribution of openings and protrusions across the mesh surface is established. The material used in forming this mesh and the amount of openings therein will define the mesh's flexibility. The flexibility of the mesh is set according to the desired end use of the article.

The porous article is created by stacking the mesh in layers, wherein the sequence of the layers is alternated so that adjacent sheets are in contact by their respective protrusions or are back-to-back. When stacked in this manner, the resulting porous structure exhibits a three-dimensional network of interconnecting pores.

Figure 1:
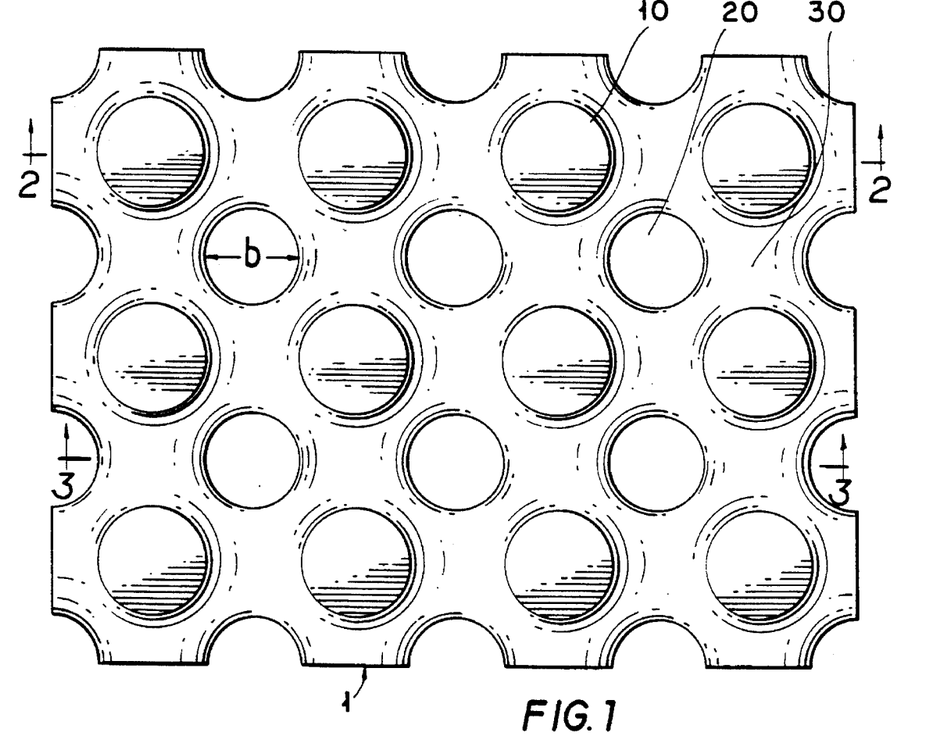
FIG. 1 provides a plan view of the mesh of the present invention.

Referring now to FIG. 1, an example of the above-noted mesh is presented. In this example, the protrusions 10 of mesh 1 have circular cross sections with a decreasing diameter that terminates with a plateau 40 of diameter "X". As can be seen, these protrusions are distributed across a substantial portion of mesh 1 in a substantially uniform coordinate grid pattern. Although a protrusion with a circular cross section is presented, other shapes may be used each having an effective diameter corresponding with that expressed in FIG. 1. In this context, the effective diameter reflects an associated structural interference preventing insertion into a corresponding opening in mesh 1.

Continuing in FIG. 1, a series of openings 20 are shown as distributed across the surface of mesh 1, in a pattern corresponding to that of the protrusions 10 but offset therefrom so that, as depicted, each opening 20 is at the center point of a rectangle defined by the four protrusions adjacent to that opening. The topographic surface resulting from this arrangement of openings and protrusions is further characterized by a series of troughs 30 extending between each pair of adjacent openings.

Figure 2:
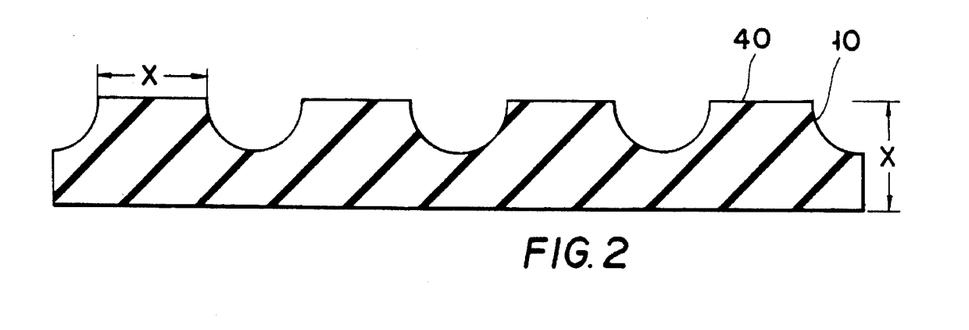
FIG. 2 provides a cross-sectional view of the mesh of FIG. 1, taken at plane 2—2.

Turning now to FIG. 2, a cross section of mesh 1 is presented as taken through the plane 2—2 of FIG. 1. As indicated in this cross-sectional slice, the thickness of the mesh at trough 30 is one-half the maximum thickness of the mesh defined by the peak of protrusion 10. In addition, the circular plateau 40 of each protrusion has a diameter equal to "X". A second cross section, taken through the plane 2—2, is presented in FIG. 3. In this cross section, the openings are circular and have a diameter equal to "Y". The trough between adjacent protrusions is represented by semicircle 32 which has an effective radius of Y/2. In the preferred embodiment, the diameter of the protrusion "X" is greater than the diameter of the opening "Y".

Figure 3:
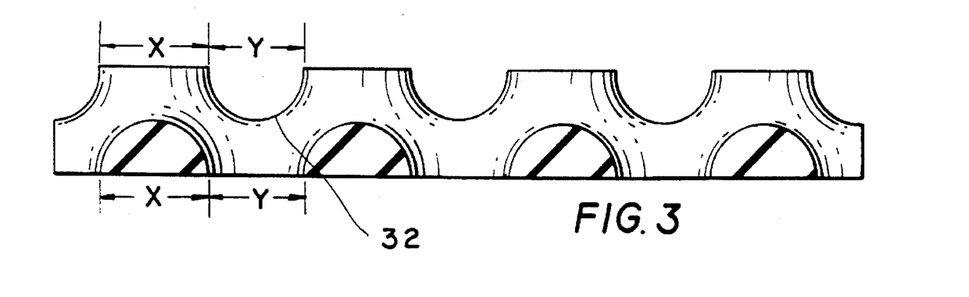
FIG. 3 provides a cross-sectional view of the mesh of FIG. 1, taken at plane 3—3.
Figure 4:
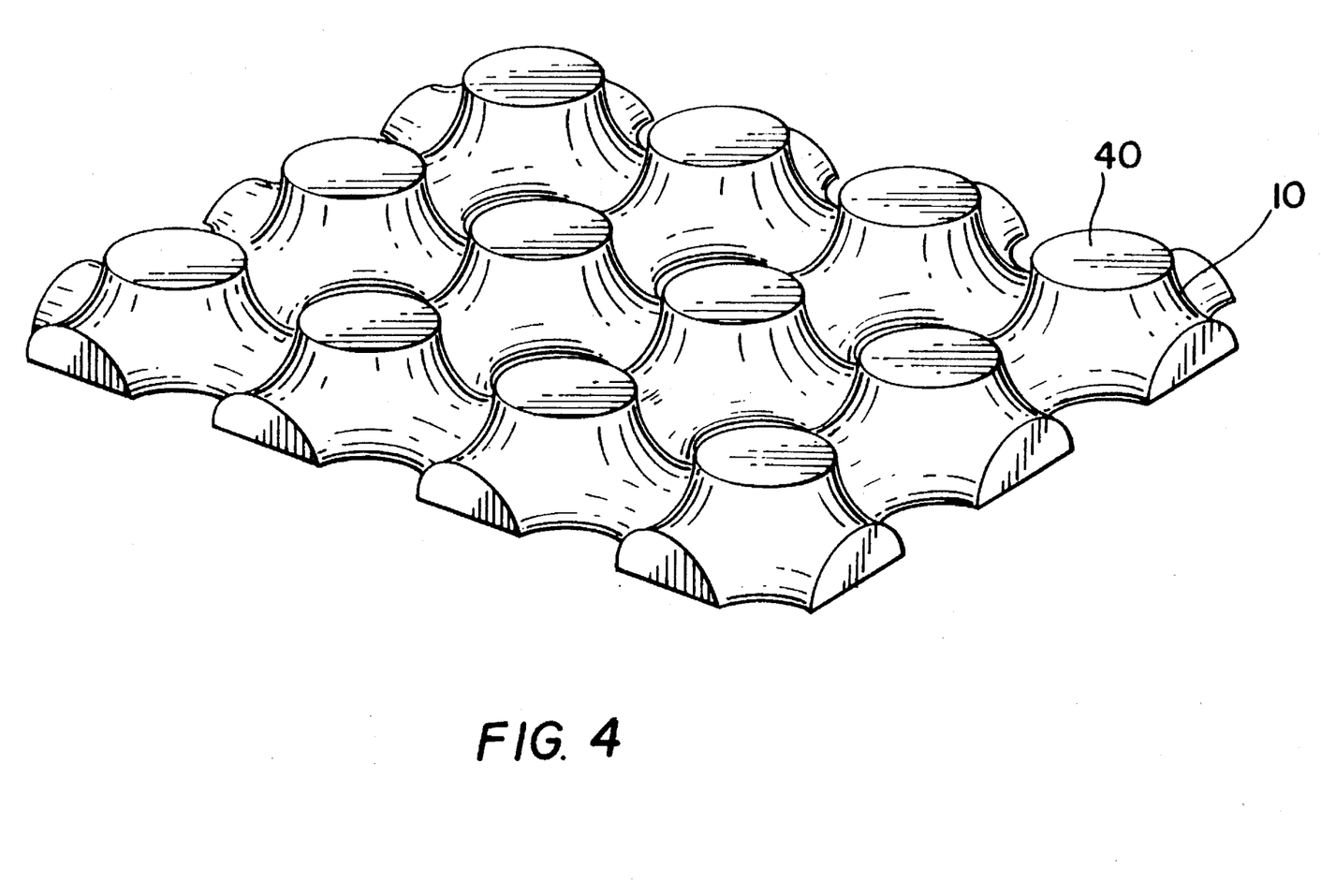
FIG. 4 provides a perspective view of the mesh of FIG. 1.

In FIG. 4, a perspective representation of the mesh structure corresponding to FIGS. 1 through 3 is presented. This particular representation reflects the topographical properties of the mesh surface as a series of integrated protrusions 10 and openings 20 positioned according to a uniform pattern. In this particular embodiment, the mesh surface is an idealized minimal surface area connecting the plateaus for each protrusion 10 with the edge of openings 20 (hidden from view in FIG. 4). This minimal surface area defines the saddle-shaped troughs 30 between each adjacent pair of openings 20.

Figure 5:
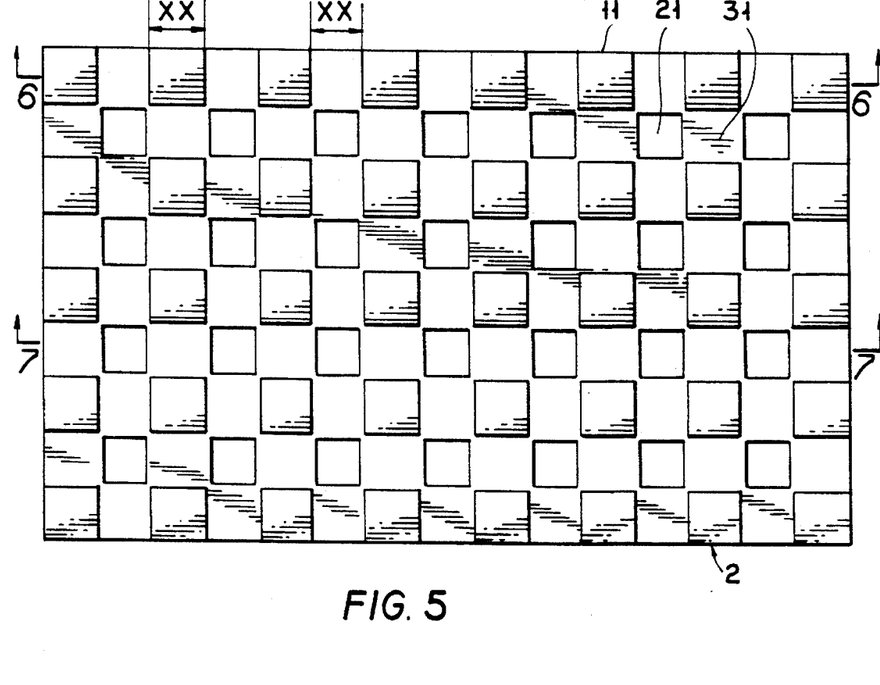
FIG. 5 provides a plan view of a second mesh structure prepared in accordance with the present invention.

Turning now to FIG. 5, a further example of the inventive mesh is presented. In this figure, the protrusions 11, openings 21 and troughs 31 are square in shape. These elements are arranged in a three-element checkerboard pattern across the surface of mesh 2, wherein adjacent openings are separated by troughs as are adjacent protrusions.

Figure 6:
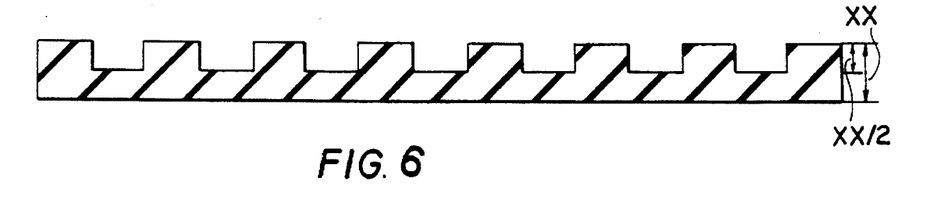
FIG. 6 provides a cross-sectional view of the mesh of FIG. 5, taken at plane 6—6.
Figure 7:
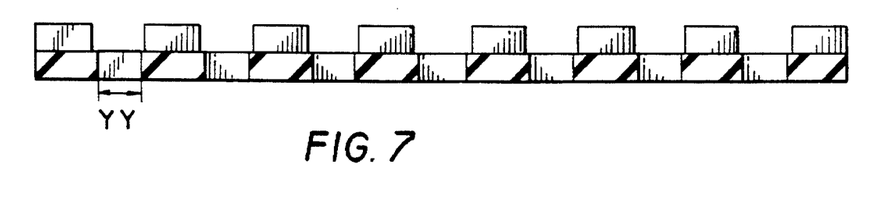
FIG. 7 provides a cross-sectional view of the mesh of FIG. 5, taken at plane 7—7.

In FIG. 6, a cross section of the mesh in FIG. 5 taken at plane 6—6 is presented, providing the relative dimensions for the protrusions 11 and troughs 31. In this arrangement, the maximum mesh thickness at protrusion 11 is "XX" and the trough thickness is "XX/2". A second cross section taken at plane 7—7 is presented in FIG. 7 indicating the relative size of openings 21 and troughs between the openings. In this arrangement, the opening width is "YY", wherein XX>YY.

Figure 8:
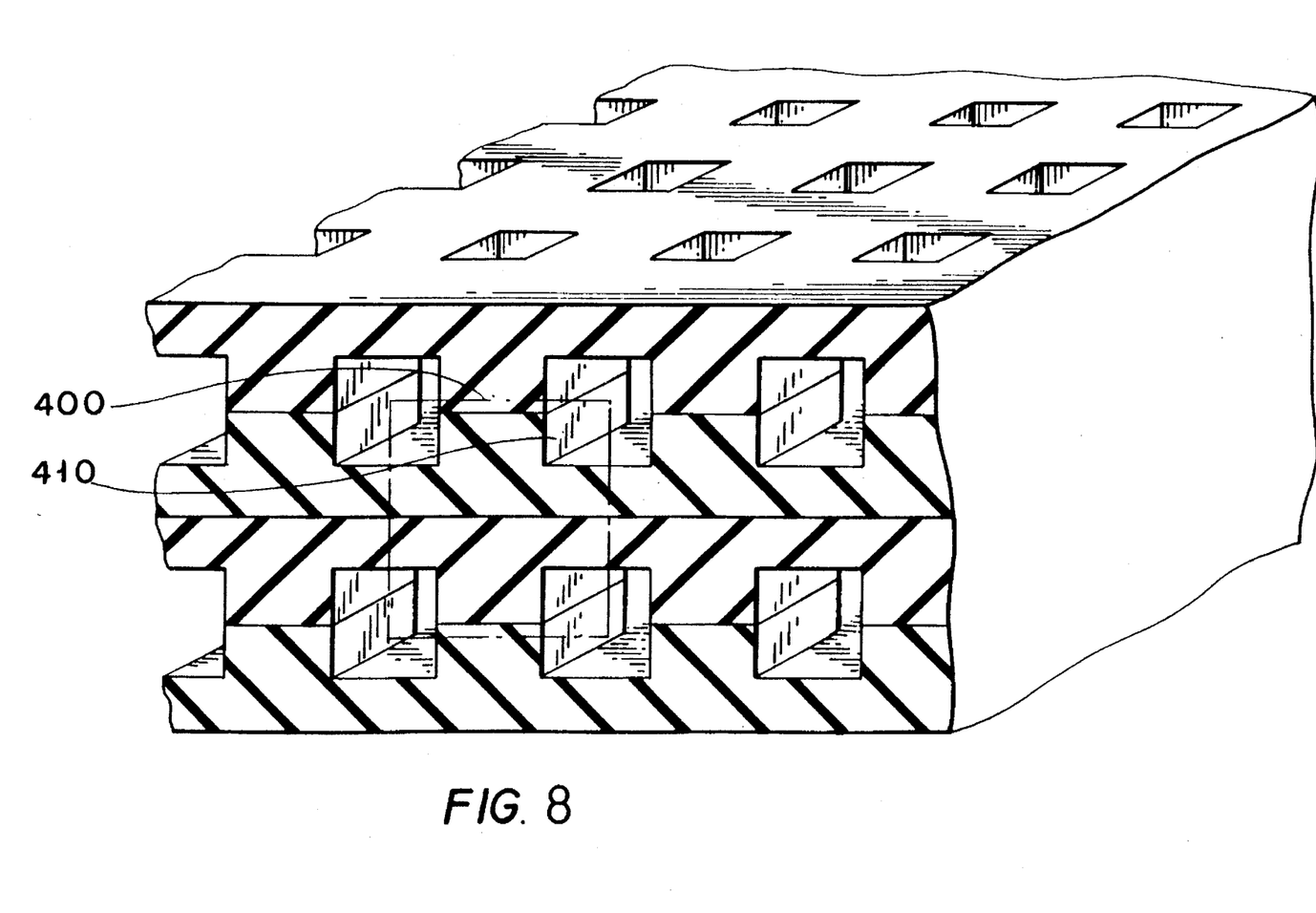
FIG. 8 provides a cross-sectional view taken through a row of protrusions for a series of alternating layers of the mesh presented in FIG. 5.

In FIG. 8, the cross section depicted in FIG. 6 is represented as layered on a mirrored image of itself. This represents the procedure for layering the mesh to build up the porous article forming a three-dimensional network of interconnecting pores. This is accomplished by taking the back-to-back mesh layers and further layering them to form a stack, wherein protrusions from one layer contact the protrusions extending from the adjacent layer. In this representation, a unit block 400 is defined as the repeating unit in the solid matrix of the porous article. More particularly, unit block 400 is interconnected to six adjacent blocks along the three orthogonal axes and by the protrusions 410, wherein two protrusions extend outward along each of the three orthogonal axes.

Figure 9A:
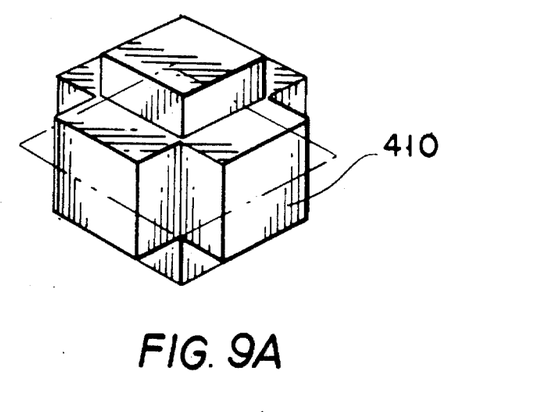
Figure 9B:
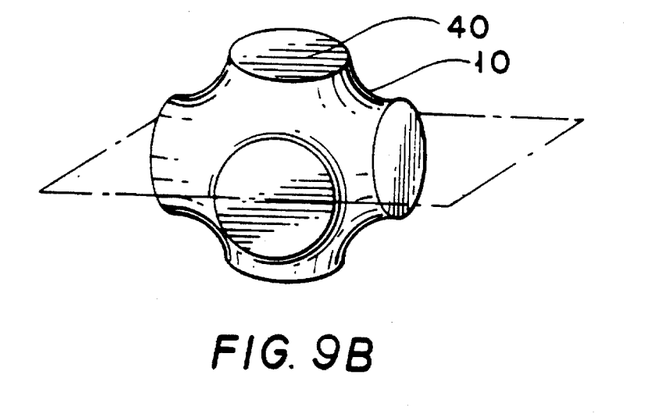
Figure 9C:
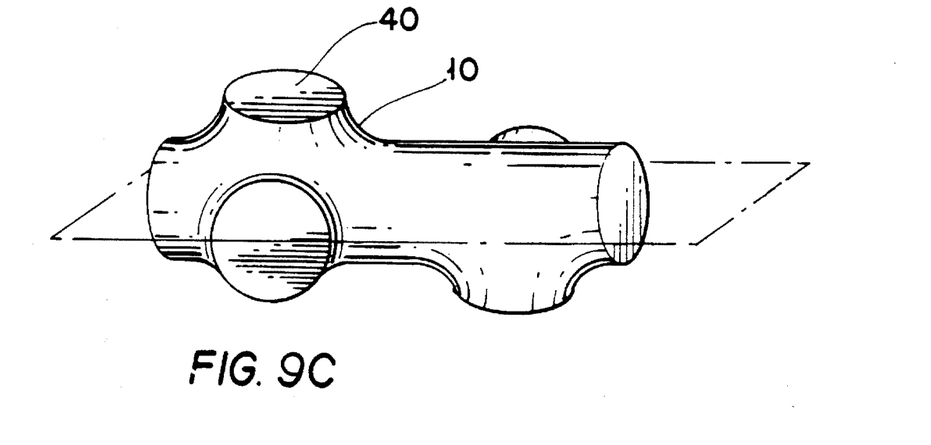

The porous structure depicted in FIG. 8 applies to a unit block of cubic form. This block is shown in isolation in FIG. 9A having cubic protrusions 410 for interconnection with adjacent blocks. For the idealized mathematically minimal surface presented in FIG. 4 and the structure resulting from layering the mesh of FIG. 4 back-to-back in a manner similar to that applied and represented in FIG. 8, the unit block will have the configuration presented in FIG. 9B. Other configurations are possible, consistent with the foregoing features. For example in FIG. 9C, a repeating unit block is depicted, wherein protrusions are offset in two of the three orthogonal planes.

Manufacturing the foregoing mesh structures may be accomplished by select micro-machining techniques. The selection of the appropriate manufacturing technique will be a function of the desired pore diameter, void volume and the selected material. In many medical applications, it is desired to form the porous articles out of a biologically acceptable material, such as silicone rubber. The use of silicone rubber provides some control over the flexibility of the resulting article making it advantageously applied to the artificial blood vessel application. Other polymers may be applied to vary the stiffness and chemical inertness of the resulting structure.

In the following example, a mesh similar to that of FIG. 4 is molded out of silicone rubber. In this process, the first step is to prepare the mold form by creating a mirror image of the desired mesh structure in the form surface. The form is prepared by taking thin sheets of steel, the thickness thereof in the range of the desired mesh thickness. This form is then coated on both sides with a photosensitive film similar to those used in conventional photolithography processes. A mask is prepared having a two-dimensional pattern of openings in a pattern corresponding to the pattern of protrusions for the resulting mesh. The photosensitive material on the top side of the steel form is partially exposed to UV light through the openings of the mask. The steel form is then stripped of the exposed photosensitive material and chemically etched in those locations stripped of the exposed film. The backside of the steel form is treated in a similar manner; thus, resulting in a series of beveled openings extending through the form and a series of protrusions extending from a single surface of the form.

This steel form is then used as a receptacle for the mesh forming polymer. This polymer is applied to the surface in uncured liquid state so that the polymer fills the void spaces of the form. The polymer is then cured forming the semi-rigid mesh structure. The final steps of this process include: deflashing the residue of the polymeric material and removing the cured polymeric mesh from the steel form. Reference is directed to the Disclosure Document identified above, which provides exemplary polymers and coating methods known in the art.

Figure 10:
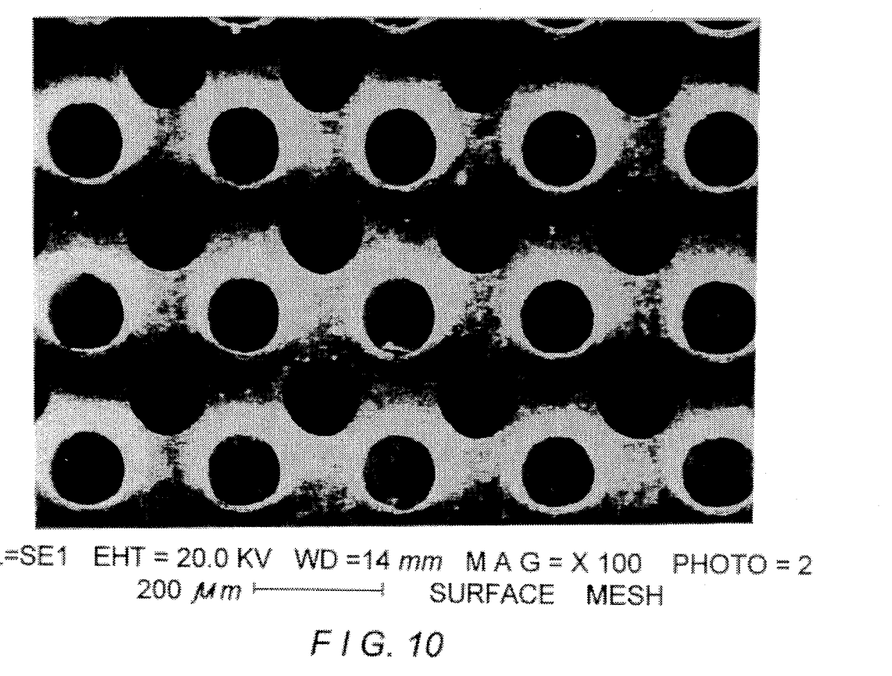
FIG. 10 provides a photograph of the surface of the form corresponding to the mesh of FIG. 1.
Figure 11:
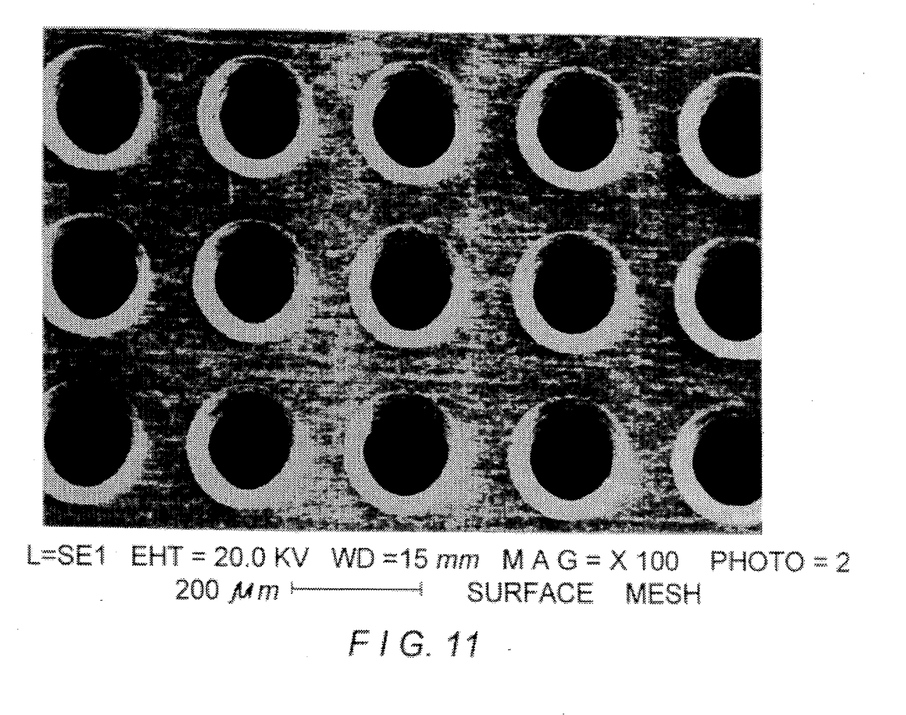
FIG. 11 provides a photograph of the bottom of the form shown in FIG. 10.

The implementation of this procedure is presented in the following sequence of photomicrographs starting with FIG. 10. The photo in FIG. 10 provides a top (plan) view of the form used to mold the mesh; this form has a structure analogous to that presented in FIG. 1. In FIG. 11, the bottom side of the steel form is shown indicating the bevels associated with each opening.

Figure 12:
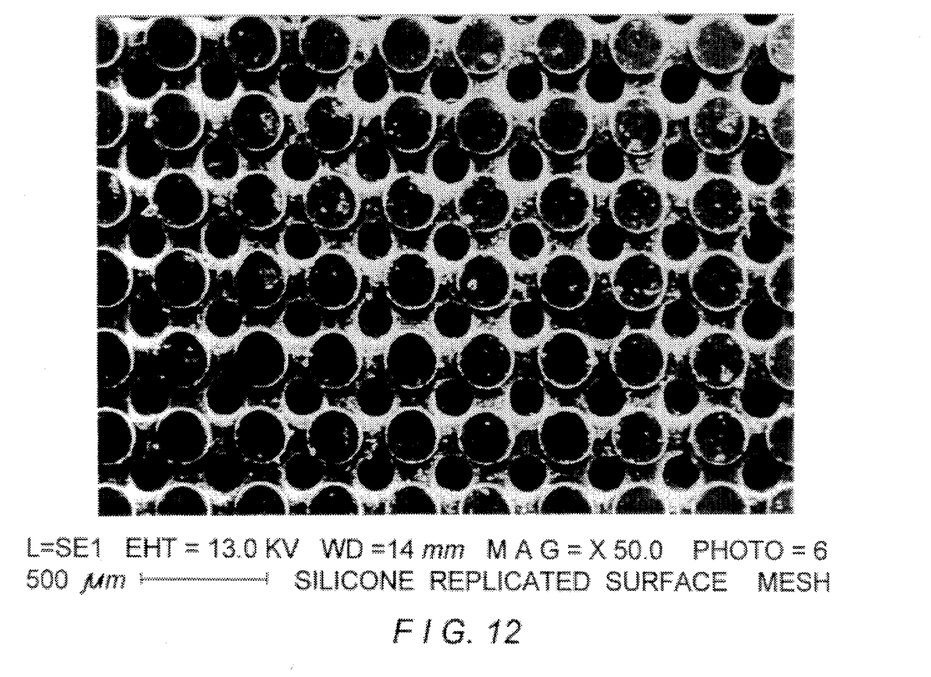
FIG. 12 provides a photograph of the surface of the mesh produced in the form of FIGS. 10 and 11.
Figure 13:
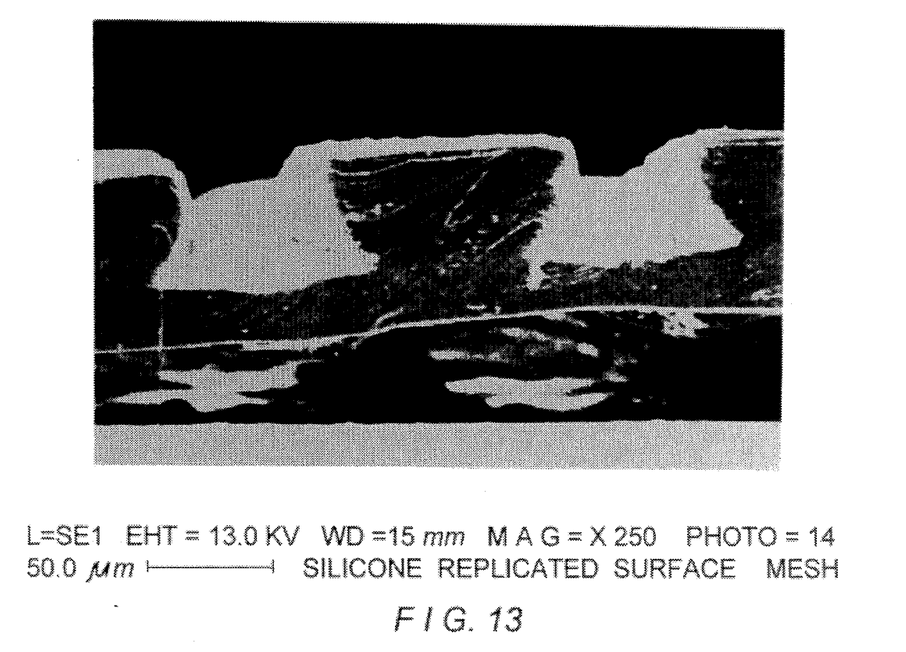
FIG. 13 provides a photograph of the protrusions extending outward from the mesh provided in FIG. 12.

The foregoing steel form is used in the manner described above to cure the mesh structure. The resulting cured mesh is shown in the photomicrograph of FIG. 12; this example using silicone rubber. As can be seen, the mesh structure has a protrusion diameter that is somewhat larger than the openings. Although the protrusions in this example provide a small deviation from the minimal surface, a mesh structure of this kind has the advantage of preventing the insertion of the protrusion into the opening of adjacent mesh layers, thus, maintaining the three-dimensional pore network. FIG. 13 provides a photomicrograph of the protrusions used in the mesh of FIG. 12.

The mesh tape provided by the above process may be used directly in the various applications discussed above. To the extent that a porous article having a defined but unusual shape is desired, this unusual shape may be created by the use of a mandrel. In this context, the tape such as depicted in FIG. 11 is wrapped around the mandrel forming a helically developed sequence of alternating layers. Adhesives may be used to fix the layers in position. The resulting shape is then removed from the mandrel and applied to its intended use.

The form shown in FIG. 10 may also be made by electron discharge machining (EDM), wherein the specific topographic surface is carved from the steel, via precision guided electron discharge.

More rigid materials will be selected for use where structural stiffness is important. An example of this would be the use of the porous article to rebuild a crushed tibia during reconstructive surgery. For this application, the porous article is made from a fine grain hydroxyapatite ceramic material in the form of the mesh presented in FIG. 4, wherein the dimensions X and Y are approximately 500 microns. A monolithic minimal surface may be formed by sintering an article of alternating plural layers of this mesh at about 1150° C. The resulting article would exhibit significant structural rigidity, a uniform three-dimensional network of interconnecting pores and a void volume approximating 50%.

The above-described arrangement is merely illustrative of the principles of the present invention. Numerous modifications and adaptations thereof will be readily apparent to those skilled in the art without departing from the spirit and scope of the present invention.

What is claimed is:

1. A non-woven porous material having a void volume percent between twenty and eighty, comprising a network of repeating interconnected blocks wherein each block has at least six protrusions extending out therefrom, and wherein said protrusions are grouped in co-planer opposing pairs aligned along each of the three orthogonal planes intersecting in the block, and further form connective arms between adjacent blocks so that substantially all of said blocks are each connected to six adjacent blocks within the body of said material thereby forming a uniform matrix of passageways aligned with said connective arms, and wherein said matrix of passageways includes saddle-shaped curved surfaces and said passageways have an effective diameter between 25 to 1000 μm.

2. The non-woven porous material of claim 1, wherein an interface of said void volume represents a mathematically minimal surface.

3. The non-woven porous material of claim 1, wherein the material is formed of silicone rubber.

4. A non-woven implantable prosthetic porous material having a void volume percent between twenty and eighty, comprising a network of repeating interconnected blocks wherein each block has at least six protrusions extending out therefrom, and wherein said protrusions are grouped in co-planer opposing pairs aligned along each of the three orthogonal planes intersecting in the block, and further form connective arms between adjacent blocks so that substantially all of said blocks are each connected to six adjacent blocks within the body of said material thereby forming a uniform matrix of passageways aligned with said connective arms, and wherein said passageways have an effective diameter between 25 to 1000 μm.

5. The non-woven porous material of claim 4, wherein said block is a cube.

6. The non-woven porous material of claim 4, wherein an interface of said void volume represents a mathematically minimal surface.

7. The non-woven porous material of claim 4, wherein the material is formed of silicone rubber.

\* \* \* \* \*